United States Patent
Jorda et al.

(10) Patent No.: US 11,802,179 B2
(45) Date of Patent: Oct. 31, 2023

(54) POLYESTERAMINES AND POLYESTERQUATS

(71) Applicant: Arkema France, Colombes (FR)

(72) Inventors: Eric Jorda, Lyons (FR); Alain Baloche, Annay (FR); Gilles Barreto, Messimy (FR); Jean-Phillippe Gillet, Brignais (FR)

(73) Assignee: Arkema France, Colombes (FR)

( * ) Notice: Subject to any disclaimer, the term of this patent is extended or adjusted under 35 U.S.C. 154(b) by 934 days.

(21) Appl. No.: 16/638,369

(22) PCT Filed: Aug. 8, 2018

(86) PCT No.: PCT/FR2018/052034
§ 371 (c)(1),
(2) Date: Feb. 11, 2020

(87) PCT Pub. No.: WO2019/034817
PCT Pub. Date: Feb. 21, 2019

(65) Prior Publication Data
US 2020/0362100 A1    Nov. 19, 2020

(30) Foreign Application Priority Data
Aug. 16, 2017   (FR) ..................................... 1757704

(51) Int. Cl.
| | | |
|---|---|---|
| *C08G 63/68* | (2006.01) | |
| *C08G 63/685* | (2006.01) | |
| *B03D 1/01* | (2006.01) | |
| *C07C 217/28* | (2006.01) | |
| *D06M 15/507* | (2006.01) | |

(52) U.S. Cl.
CPC .......... *C08G 63/6856* (2013.01); *B03D 1/011* (2013.01); *C07C 217/28* (2013.01); *D06M 15/507* (2013.01); *B03D 2201/02* (2013.01)

(58) Field of Classification Search
None
See application file for complete search history.

(56) References Cited

U.S. PATENT DOCUMENTS 4,606,916 A    8/1986   Hofinger et al.

FOREIGN PATENT DOCUMENTS

| EP | 0035263 | A2 | 9/1981 |
| EP | 0144975 | A2 | 6/1985 |
| JP | 2811433 | B2 | 10/1998 |
| WO | 2008089906 | A1 | 7/2008 |
| WO | 2011000895 | A1 | 1/2011 |
| WO | 2011147855 | A2 | 12/2011 |
| WO | 2012028542 | A1 | 3/2012 |

OTHER PUBLICATIONS

International Search Report and Written Opinion for International Application No. PCT/FR2018/052034, dated Oct. 1, 2018, 7 pages.

*Primary Examiner* — Peter Keyworth
(74) *Attorney, Agent, or Firm* — RatnerPrestia

(57) ABSTRACT

Provided is a compound which may be obtained by esterification condensation of components as described herein. The compound may be used as a collector for ore enrichment (flotation), as a corrosion inhibitor, as a viscosity enhancer, emulsifier or stabilizer that is useful for the oil and gas industry, as a clay modifier, as an adhesion promoter, as an antiagglomerant additive, as an additive in haircare products, as a fabric softener, as an antistatic agent in polymers, as a bitumen emulsion additive, as a detergency cationic agent, as a fertilizer additive, as an antiagglomerant for hydrates, as a lubrication or adhesion-promoting additive, for example.

17 Claims, No Drawings

POLYESTERAMINES AND POLYESTERQUATS

CROSS-REFERENCE TO RELATED APPLICATIONS

This is the national phase of International Application No. PCT/FR2018/052034, filed 8 Aug. 2018, which claims priority to French Application No. 1757704, filed 16 Aug. 2017. The disclosure of each of these applications is incorporated herein by reference in its entirety for all purposes.

FIELD OF THE INVENTION

The present invention relates to compounds having polyesteramine and polyesterquat structures. Such structures are novel and compounds with such a structure may be used in many fields of application, for example as surfactants, as corrosion inhibitors and the like.

BACKGROUND OF THE INVENTION

Fatty alkylamines and quaternary ammonium compounds are particularly useful chemical substances that are employed in a wide variety of industries. Among all the possible applications, mention may be made of their use as biocides, haircare products, textile softeners or antistatic additives for plastics. Their strong adsorption properties on mineral or metal surfaces or other solid particles make them particularly advantageous as wetting agents, corrosion inhibitors, collectors for ore enrichment, acidic attack additive for phosphate rock, fertilizer and surface or internal treatment additive for mineral salts, antiagglomerants for hydrates, clay modifiers, lubrication additives or adhesion promoters. They may also have viscosity-enhancing, emulsifying, or stabilizing properties that are useful for the oil and gas industry (demulsifiers, surfactants for enhanced oil recovery, surfactants for fracturing fluids, surfactants for acidifying fluids, surfactants for improving the injectability of produced water, surfactants for drilling muds), the bitumen emulsion industry or for detergency.

These fatty alkylamines and quaternary ammonium compounds are well known in industry and the search to find new products is ongoing. In the course of the last 30 years, another family of nitrogen-based compounds of higher molecular weight has been described in the literature. These compounds are amines and a quaternary ammonium with a polymeric or oligomeric structure.

For example, EP 0 035 263 describes a product of reaction between a dicarboxylic acid and an ethoxylated fatty amine, said product being used as a textile softener. In EP 0 144 975, the same reaction product may be quaternized and used as a hair conditioner.

Patent application WO 2008/089906 describes a product of reaction of a fatty acid with a diacid and an (alkyl)polyethanolamine, said reaction product then being quaternized and used as a collector for the flotation of non-sulfide ore.

Similarly, JP08-291281 describes products of reaction of alkoxylated $C_1$-$C_{22}$ alkylamines with diacids (or anhydrides) followed by a quaternization reaction, said products being used as antistatic agents in composite resins, in particular for the motor vehicle industry.

WO 2011/147855 also describes a product of reaction of a fatty alcohol with a diacid and an (alkyl)polyethanolamine, optionally followed by a partial or total quaternization reaction, such a product typically being used for floating silicates. The fatty alcohol may be replaced with an alkylated fatty amine including only one alkoxylated chain with only one —OH end function.

Consequently, there is still a need for novel cationic oligomeric or polymeric compounds for use in the fields of application mentioned above, said compound being more easily prepared, more stable, less expensive to synthesize and also having better environmental properties in terms of toxicity and biodegradability, and having improved technical performance qualities.

Consequently, the present invention relates to a compound which may be obtained by esterification condensation of:
A/ an alkoxylated fatty amine of formula (I), or the product of partial or total quaternization of said alkoxylated fatty amine of formula (I):

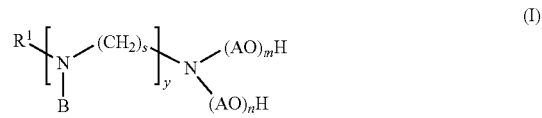

in which:
$R^1$ is chosen from a hydrocarbyl group containing 8 to 24 carbon atoms, preferably 10 to 24 and more preferably 12 to 24 carbon atoms, and a group of formula $R^4$—O-(A'O)$_w$-T-, in which $R^4$ is a hydrocarbyl group containing 8 to 24 carbon atoms and preferably 12 to 24 carbon atoms, w represents an integer in the range from 0 to 20, preferably from 0 to 10, more preferably from 0 to 6 and even more preferably from 0 to 4, A'O is an alkylenoxy group containing 2 to 4 carbon atoms, preferably 2 or 3 carbon atoms, more preferably 2 carbon atoms; T is alkylene with 1 to 6 carbon atoms, preferably 1 to 4 carbon atoms and most preferably 2 or 3 carbon atoms, AO is an alkylenoxy group containing 2 to 4 carbon atoms, preferably 2 or 3 carbon atoms, more preferably 2 carbon atoms, B is chosen from a $C_1$-$C_4$ alkyl, an aryl and an arylalkyl (for example phenyl or phenylalkyl, such as benzyl) group, m represents an integer between 1 and 20, preferably between 1 and 10, more preferably between 1 and 6, and even more preferably between 1 and 4, limits inclusive, n represents an integer between 1 and 20, preferably between 1 and 10, more preferably between 1 and 6, and even more preferably between 1 and 4, limits inclusive, s is 1, 2 or 3, preferably 2 or 3, and y is an integer from 0 to 5, preferably from 0 to 3, more preferably y is 0 or 1, even more preferably y is 0, B/ with a dicarboxylic acid, or a derivative thereof, of formula (II):

in which
D is chosen from —F, —Cl, Br and —OR$^3$, in which R$^3$ is hydrogen or a C$_1$-C$_4$ alkyl group,
R$^2$ is chosen from the group constituted by:
a direct bond,
a linear or branched, saturated or unsaturated C$_1$-C$_{20}$ hydrocarbon-based chain optionally substituted with one or more —OH groups, preferably an alkylene radical of formula —(CH$_2$)$_z$—, in which z is an integer from 1 to 20, preferably from 1 to 10, preferably from 2 to 6 and most preferably equal to 4, a substituted alkylene radical, said alkylene radical being substituted with 1 or 2 —OH groups, an alkenylene radical containing from 1 to 20 and preferably from 1 to 10 carbon atoms, a substituted alkenylene radical, said alkenylene radical being substituted with 1 or 2 methyl and/or methylene groups,
a cycloalkylene group,
cycloalkenylene and
arylene
C/ with an (alkyl)alkanolamine of formula (III) derivative or product of partial or total quaternization of said (alkyl) alkanolamine derivative of formula (III):

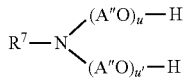

(III)

in which:
A″O represents an alkylenoxy group containing from 2 to 4 carbon atoms, preferably 2 or 3 carbon atoms, more preferably 2 carbon atoms,
u represents an integer between 1 and 20, preferably between 1 and 10, more preferably between 1 and 6, and even more preferably between 1 and 4, limits inclusive,
u′ represents an integer between 1 and 20, preferably between 1 and 10, more preferably between 1 and 6, and even more preferably between 1 and 4, limits inclusive,
R$^7$ is chosen from a hydrocarbyl group containing 1 to 7, preferably 1 to 6 carbon atoms, more preferably 1 to 4 carbon atoms, an aryl or arylalkyl group (for example, a phenyl or naphthyl group), a group of formula H—(OA″)$_v$-(in which v represents an integer between 1 and 20, preferably between 1 and 10, more preferably between 1 and 6, and even more preferably between 1 and 4, limits inclusive), HO(CH$_2$)$_q$—, and a group of formula (IV):

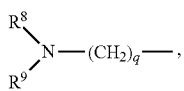

(IV)

in which R$^8$ and R$^9$, which may be identical or different, are chosen from a hydrocarbyl group containing 1 to 6 carbon atoms, preferably 1 to 4 carbon atoms, and q is an integer from 1 to 10, preferably from 2 to 6, limits inclusive, and most preferably q is 2 or 3,
or R$^8$ and R$^9$, together with the nitrogen atom to which they are attached, form a 5-, 6- or 7-membered ring, optionally including one or more heteroatoms chosen from oxygen, nitrogen and sulfur.

SUMMARY OF THE INVENTION

In the present description, the term "hydrocarbyl" denotes a linear or branched, saturated or unsaturated hydrocarbyl chain.

DETAILED DESCRIPTION OF THE INVENTION

In a preferred embodiment, compounds of the invention may be obtained by esterification condensation as defined above, in which, in the fatty amine of formula (I), R$^1$ includes 8 or more than 8 carbon atoms, typically from 8 to 24 carbon atoms, preferably from 10 to 24, more preferably from 12 to 24 carbon atoms, limits inclusive, and in the (alkyl)alkanolamine derivative of formula (III), R$^7$ includes 6 carbon atoms or less, typically from 1 to 6 carbon atoms, more preferably 1 to 4 carbon atoms, limits inclusive.

In an even more preferred embodiment, compounds of the invention may be obtained by esterification condensation as defined above, in which, in the fatty amine of formula (I) and in the (alkyl)alkanolamine derivative of formula (III), R$^1$ and R$^7$ are such that the difference in the number of carbon atoms they include is greater than 2, typically from 2 to 23, preferably from 5 to 23, more preferably from 10 to 23, limits inclusive.

It is understood that the dicarboxylic acids or derivatives thereof of formula (II) also comprise the corresponding anhydride forms thereof. It is also understood that when the alkylenoxy chain contains more than one alkylenoxy group, the alkylenoxy groups may be identical or different. Similarly, when y is greater than 1, the repeating units may be identical or different.

The present invention also relates to the compound of the present invention (which may be obtained by reaction between the alkoxylated fatty amine of formula (I), the dicarboxylic acid or a derivative thereof of formula (II), and the (alkyl)alkanolamine derivative of formula (III)), after additional reaction in which some or all of the nitrogen atoms are quaternized by reaction with a reagent of formula R$^5$X, in which R$^5$ is chosen from a C$_1$-C$_6$ hydrocarbyl group, preferably a C$_1$-C$_4$ alkyl, a phenyl or a phenylalkyl, such as benzyl, group, and X is any leaving group known in the art, and preferably, X is generally chosen from halogens, sulfates, carbonates, and the like.

Formula (1) below is one possible representation of the compounds of the present invention, as described above, which may be obtained by the esterification condensation of the alkoxylated fatty amine of formula (I) (comprising its partial or total quaternization product), with the dicarboxylic acid, or a derivative thereof, of formula (II), and with an (alkyl)alkanolamine derivative of formula (III) (comprising its partial or total quaternization product).

Consequently, and in a second aspect, the present invention relates to a compound of general formula (1):

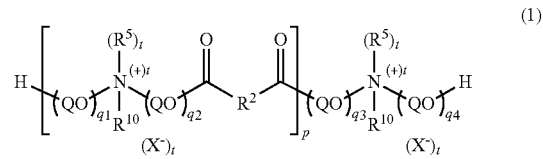

(1)

in which:
R², R⁵ and X are as defined above,
t is 0 or 1,
p is an integer in the range from 1 to 15, preferably from 1 to 10, more preferably from 1 to 5, limits inclusive,
QO represents an alkylenoxy group containing from 2 to 4 carbon atoms, preferably 2 or 3 carbon atoms, more preferably 2 carbon atoms, given that all the Q groups present in the compound of formula (1) may be identical or different,
$q_1$, $q_2$, $q_3$ and $q_4$, which may be identical to or different from each other, each represent an integer between 1 and 20, preferably between 1 and 10, more preferably between 1 and 6 and even more preferably between 1 and 4, limits inclusive,
each group $R^{10}$, independently of the others, represents $R^7$ as defined previously or a group $R^1$-(G)$_y$-in which $R^1$ and y are as defined previously and G represents a group of formula (IV):

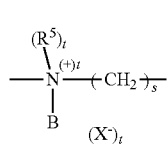

(IV)

in which B, $R^5$, X, t and s are as defined above, the group $(CH_2)_s$ is a spacer between the two nitrogen atoms to which it is attached,
given that at least one of the groups $R^{10}$ represents $R^7$, and at least one other of the groups $R^{10}$ represents $R^1$-(G)$_y$- and each t is independent of the others.

In one particular embodiment, the alkoxylated fatty amine of formula (I) is of formula (IA):

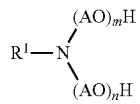

(IA)

which is the alkoxylated fatty amine of formula (I) in which y represents 0 and $R^1$, AO, m and n are as defined above, and also the corresponding partially or totally quaternized derivatives thereof.

In another particular embodiment, the (alkyl)alkanolamine derivative of formula (III) is of formula (IIIA):

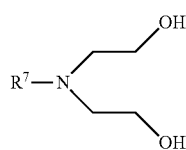

(IIIA)

which is the (alkyl)alkanolamine of formula (III) in which u and u' each represent 1, A"O is ethylenoxy and $R^7$ is as defined above. In the compound of formula (IIIA) above, $R^7$ is preferably a hydrocarbyl group containing 1 to 4 carbon atoms. The compound of formula (IIIA) above also covers the corresponding partially or totally quaternized derivatives thereof.

The dicarboxylic acid derivative, derivative of general formula (II), described may be a dicarboxylic acid or any dicarboxylic acid derivative or anhydride known to those skilled in the art, and typically a dicarboxylic acid, a dicarboxylic acid halide, for example a chloride, a dicarboxylic acid diester, or a cyclic anhydride of a dicarboxylic acid. The derivatives that are the most suitable are the dicarboxylic acids and the corresponding cyclic anhydrides thereof.

Illustrative examples of dicarboxylic acid derivatives of general formula (II) comprise oxalic acid, malonic acid, succinic acid, glutaric acid, glutaconic acid, adipic acid, muconic acid, pimelic acid, phthalic acid and isomers thereof, tetrahydrophthalic acid, malic acid, maleic acid, fumaric acid, suberic acid, mesaconic acid, sebacic acid, azelaic acid, tartaric acid, itaconic acid, glutinic acid, citraconic acid, brassylic acid, dodecanedioic acid, traumatic acid, thapsic acid, the corresponding acid chlorides thereof, the corresponding methyl or ethyl esters thereof, and the corresponding cyclic anhydrides thereof, and also mixtures thereof.

Preferred dicarboxylic acid derivatives of general formula (II) are chosen from oxalic acid, malonic acid, succinic acid, glutaric acid, adipic acid, pimelic acid, phthalic acid and isomers thereof, tetrahydrophthalic acid, malic acid, tartaric acid, itaconic acid, the corresponding acid chlorides thereof, the corresponding methyl or ethyl esters thereof, and the corresponding cyclic anhydrides thereof, and also mixtures thereof.

Alkoxylated fatty amines of formula (I) are available or may be prepared according to a process known in the literature, and may be readily prepared, for example, by alkoxylation of fatty amines of formula (a):

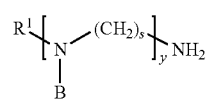

(a)

in which $R^1$, B, s and y are as defined above.

Illustrative examples of suitable fatty amines according to formula (a) for use as starting materials for the preparation of alkoxylated fatty amines of formula (I) comprise, but are not limited to, fatty amines of formula (a1) in which y represents 0 and fatty amines of formula (a2) in which y represents 1, s represents 3 and B represents methyl:

(a1)

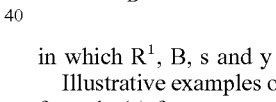

(a2)

in which $R^1$ is as defined above.

Particular examples of amines of formula (a1) are amines of formula (a3):

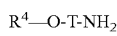

R⁴—O-T-NH₂    (a3), in which $R^4$ and T are as defined above and w is 0.

More specific examples of the amines of formula (a) mentioned above comprise, but are not limited to, 2-ethylhexylamine, 2-propylheptylamine, n-octylamine, n-decylamine, n-dodecylamine, (coconut-alkyl)amine, (palm oil-alkyl)amine, n-tetradecylamine, n-hexadecylamine, n-octadecylamine, oleylamine, (tallow-alkyl)amine, (hydrogenated tallow-alkyl)amine, (rapeseed-alkyl)amine, (soybean-alkyl)amine, erucylamine, N-(n-decyl)-N-methyltrimethylenediamine, N-(n-dodecyl)-N-methyltrimethylenediamine, N-(coconut-alkyl)-N-methyltrimethylenediam ine, N-(rapeseed-alkyl)-N-methyltrimethylenediamine, N-(soybean-alkyl)-N-methyltrimethylenediamine, N-(tallow-alkyl)-N-methyltrimethylenediamine, N—(hydrogenated tallow-alkyl)-N-methyltrimethylenediamine, N-erucyl-N-methyltrimethylenediamine and isotridecyloxypropylamine, and also mixtures thereof.

According to one embodiment of the invention, the amines mentioned above are fatty amines obtained from natural acids or oil (plant or animal) and mixtures thereof, for example coconut fatty acids, tallow fatty acids, rapeseed oils, soybean oils and palm oils.

These fatty amines are then typically alkoxylated with 2 to 40, preferably 2 to 20, more preferably 2 to 12 and even more preferably 2 to 8 EO (ethylene oxide units), and/or 2 to 40, preferably 2 to 20, more preferably 2 to 12 and even more preferably 2 to 8 PO (propylene oxide units), and/or 2 to 40, preferably 2 to 20, more preferably 2 to 12 and even more preferably 2 to 8 BO (butylene oxide units). Blocks with EO are generally added first and PO and/or BO last, or blocks with PO and/or BO added first and EO last, or with mixtures of EO and PO and/or BO to produce alkoxylated products randomly of general formula (I). The alkoxylation may be performed via any suitable process known in the art using, for example, an alkaline catalyst, such as potassium hydroxide (KOH) or an acid catalyst or even without catalyst.

Examples of marketed products of formula (I) comprise Noramox® SD20, Noramox® SD15, Noramox® S11, Noramox® S5, Noramox® S7, Noramox® S2, Noramox® SH2, Noramox® O2, Noramox® O5, Noramox® C2, Noramox® C5 and Noramox® C15. All these marketed products are available from CECA S.A. Other examples of marketed products of formula (I) comprise Tomamine® E-17-5 and Tomamine® E-T-2, sold by Air Products.

(Alkyl)alkanolamine derivatives of formula (III) are available or may be prepared according to a process described in the literature. Illustrative examples of suitable (alkyl)alkanolamine derivatives of formula (III) comprise, but are not limited to, triethanolamine, methyldiethanolamine, ethyldiethanolamine, propyldiethanolamine, butyldiethanolam ine, isobutyldiethanolam ine, pentyldiethanolam ine, phenyldiethanolamine, hexyldiethanolamine, heptyldiethanolamine, and also the corresponding alkoxylation products thereof.

Other examples of amines that are suitable as starting materials for the preparation of alkoxylated derivatives of formula (III) comprise, without limitation, methylamine, ethylamine, propylamines, butylamines, pentylamines, hexylamines, heptylam ines, dimethylam inoethylam ine, diethylam inoethylamine, dimethylamino-propylamine (DMAPA), diethylaminopropylamine (DEAPA), dipropylamino-propylamine, dibutylaminopropylamine (DBAPA), 1-(3-aminopropyl)-2-pyrrolidine, 3-morpholinopropylamine, 1-(3-aminopropyl)piperidine and 1-(3-aminopropyl)-pipecoline. Some of these alkoxylated derivatives of formula (III) are new and, as such, form part of the present invention.

A suitable process for preparing the products for use in the present invention comprises the steps of mixing at least one compound of formula (II) with at least one compound of formula (III) as defined above and at least one compound of formula (I) as defined above, and performing an esterification condensation reaction between the compounds in the mixture.

As will be apparent to a person skilled in the art, other processes in which compounds of formulae (I), (II) and (III) react sequentially with each other in various orders are also suitable. For example, it is possible to perform an esterification condensation reaction between compounds of formulae (I) and (II) in a first stage, and then to perform another esterification condensation reaction of this condensation product with a compound of formula (III) in an additional step. Another suitable process involves performing an esterification condensation reaction between compounds of formulae (II) and (III) in a first stage, and then performing another esterification condensation reaction of this condensation product with a compound of formula (I) in an additional step.

Other alternative processes involve performing an esterification condensation reaction, for instance between:
  a. a product of condensation reaction between compounds of formulae (II) and (III) and
  b. a product of condensation reaction between compounds of formulae (I) and (II)
  c. optionally performing another esterification condensation reaction of the reaction product compounds of step a and step b above together with at least one compound of formula (I) and/or formula (II) and/or formula (III).

More generally, the compounds of formula (1) of the present invention may be prepared from esterification condensation reaction(s) in which at least one compound of formula (I) and at least one compound of formula (II) and at least one compound of formula (III) react in one or more simultaneous and/or sequential and/or alternating esterification condensation reactions.

The esterification condensation reaction which takes place between the compounds of formula (II) and of formulae (I) and (III) is a reaction that is known per se in the art. The reaction is preferably performed in the presence of an esterification catalyst, such as a Brønsted acid or a Lewis acid, for example methanesulfonic acid, para-toluenesulfonic acid, hypophosphoric acid, citric acid or boron trifluoride ($BF_3$).

When a dicarboxylic acid derivative of formula (II), in which D is O—$R^3$, is used, the reaction is a transesterification, which, as a variant, may be performed in the presence of an alkaline catalyst. As a variant, other conventional techniques known to those skilled in the art may be used starting with other dicarboxylic acid derivatives, for example starting with the anhydrides thereof or the acid chlorides thereof.

As will be apparent to a person skilled in the art, the various esterification reactions may be performed with or without addition of solvents. If solvents are present during the reaction, the solvents must be inert with respect to the esterification, for example toluene or xylene, and the like.

The esterification condensation reaction between the components (I), (II) and (III) may be performed at any temperature under known operating conditions, and, for example, at a temperature typically within the range from 60° C. to 300° C., preferably from 120° C. to 280° C., and generally for a time within the range from 1 hour to several hours, preferably from 2 hours to 20 hours. The esterification condensation reaction may be performed at atmospheric pressure; as a variant, said reaction may optionally be performed at a reduced pressure, for example from 500 Pa to 20 000 Pa.

In one specific embodiment of the present invention, the mole ratio between the reagents [(I)+(III)] and (II) is from 2:1 to 1:2, preferably from 1.5:1 to 1:1.5 and most preferably from 1.4:1 to 1:1.4.

According to another specific embodiment of the present invention, the mole ratio between the reagents [(I)+(III)] and (II) is from 2:1 to 1:1, preferably from 2:1 to 1.2:1 and most preferably from 2:1 to 1.3:1.

According to another additional embodiment, the mole ratio between (I) and (III) is from 15:1 to 1:15, preferably from 10:1 to 1:10, more preferably from 4:1 to 1:4 and most preferably from 2:1 to 1:2.

When a quaternary product is desired, the preparation process may also comprise at least one step consisting in adding an alkylating agent to the condensation reaction product and performing said quaternization reaction on the condensation product, according to techniques known in the art.

Per se, when all the t are 0 in formula (1), the product is a tertiary polyesteramine compound, and when all the t are 1, the product is a quaternary polyammonium polyester compound, resulting from the quaternization of the compound in which t is 0. As will be apparent to a person skilled in the art, when some of the t are 0 and some of the t are 1, the product is a partially quaternized polyesteramine compound.

For the quaternization reaction step, the preferred alkylating agents are chosen from compounds of formula $R^5X$. Illustrative examples of such alkylating agents comprise, but are not limited to, methyl chloride, methyl bromide, methyl iodide, dimethyl sulfate, diethyl sulfate, dimethyl carbonate and benzyl chloride, the alkylating agents that are the most preferred being methyl chloride, dimethyl sulfate, diethyl sulfate or benzyl chloride and mixtures thereof, preferably methyl chloride and/or dimethyl sulfate.

According to one variant, the quaternization may be performed on the fatty amine of formula (I) and/or on the (alkyl)alkanolamine derivative of formula (III) before performing the esterification condensation reaction(s) with the dicarboxylic acid or a derivative thereof of formula (II). Other variants comprise the quaternization reaction on the intermediate compounds obtained during the sequential or alternating esterification condensation reactions. One or more total or partial quaternization reactions may be performed after any one of these intermediate steps.

The quaternization reactions are generally performed in water and/or in one or more organic solvents, such as ethanol, isopropanol (IPA), ethylene glycol monobutyl ether, di(ethylene glycol) monobutyl ether (BDG), monoethylene glycol (MEG), diethylene glycol (DEG), or mixtures thereof. The preferred solvents are chosen from isopropanol (IPA), ethanol, and mixtures thereof.

The temperature of the quaternization reaction is, appropriately, in the range from 20° C. to 100° C., preferably at least 40° C., more preferably at least 50° C., and most preferably at least 55° C., and preferably not more than 90° C. The quaternization reaction is typically performed to a time within the range from several tens of minutes to several tens of hours, preferably from 1 hour to 100 hours, more preferably from 1 hour to 30 hours.

The quaternization reaction may be partial or total. The quaternization reaction is generally monitored by means of reducing the total alkalinity of the reaction medium. "Total quaternization" is obtained when the total alkalinity value is less than or equal to 0.2 meq/g, preferably less than or equal to 0.1 meq/g, more preferably less than or equal to 0.05 meq/g, as measured by titration with hydrochloric acid.

In one embodiment, the preferred compounds of formula (1) are those in which:
$R^2$ is chosen from the group consisting of a divalent hydrocarbyl radical containing from 1 to 10, preferably from 2 to 6 and most preferably 4 carbon atoms, limits inclusive,
when $R^{10}$ is $R^7$, $R^7$ is chosen from a hydrocarbyl group containing 1 to 4 carbon atoms, preferably 1 to 2 carbon atoms and most preferably $R^7$ is methyl,
when $R^{10}$ is $R^1$-(G)y-, y=0 and $R^1$ is chosen from a hydrocarbyl group containing 8 to 24 carbon atoms, preferably 12 to 24 carbon atoms,
QO represents an ethoxy group and
p, $q_1$, $q_2$, $q_3$, $q_4$, t and $R^5$ are as defined above.

According to another embodiment, preferred compounds of formula (1) are those in which all the "t" are equal to 1, i.e. all the nitrogen atoms are quaternized (which means "total quaternization"), all the other variable groups and integers being as defined above.

According to another embodiment, preferred compounds of formula (1) are those in which all the "t" are equal to 1 and $R^5$ is chosen from methyl and ethyl, all the other variable groups and integers being as defined above.

According to another additional embodiment, preferred compounds of formula (1) are those in which all the "t" are equal to 1, $R^5$ is chosen from methyl and ethyl, and X is chosen from halogens and sulfates (for example methosulfates), all the other variable groups and integers being as defined above.

According to another embodiment, preferred compounds of formula (1) are those in which $q_1$, $q_2$, $q_3$ and $q_4$, independently of each other, are identical or different, and are chosen from 1, 2, 3, 4, 5 and 6, p is in the range from 1 to 10, limits inclusive, and all the other variable groups and integers are as defined above.

Particularly preferred compounds of formula (1) according to the present invention are those obtained by simultaneous/sequential/alternating esterification condensation reaction(s) of:
at least one compound of formula (I), in which y=0 and $R^1$ is chosen from a hydrocarbyl group containing 8 to 24 carbon atoms, preferably 10 to 24 and more preferably 12 to 24 carbon atoms,
at least one compound of formula (II), and
at least one compound of formula (III), in which $R^7$ is a hydrocarbyl group containing 1 to 7 and preferably 1 to 6 carbon atoms, more preferably 1 to 4 carbon atoms,
and also the products of partial or total quaternization reaction thereof.

The most preferred compounds of formula (1) according to the present invention are those obtained by simultaneous/sequential/alternating esterification condensation reaction(s) of:
at least one compound of formula (I), in which y=0 and $R^1$ is chosen from a hydrocarbyl group containing 8 to 24 carbon atoms, preferably 10 to 24 and more preferably 12 to 24 carbon atoms and AO is ethoxy,
at least one compound of formula (II), and
at least one compound of formula (III), in which $R^7$ is a hydrocarbyl group containing 1 to 7 and preferably 1 to 6 carbon atoms, more preferably 1 to 4 carbon atoms, and A"O is ethoxy,
and also the products of partial or total quaternization reaction thereof.

Most particularly preferred compounds of formula (1) according to the present invention are those obtained by simultaneous/sequential/alternating esterification condensation reaction(s) of:
- at least one compound of formula (I), in which y=0 and $R^1$ is chosen from a hydrocarbyl group containing 8 to 24 carbon atoms, preferably 10 to 24 and more preferably 12 to 24 carbon atoms, AO is ethoxy, and m and n, independently of each other, which may be identical or different, represent an integer between 1 and 10, preferably 1 to 6, more preferably 1 to 4, limits inclusive,
- at least one compound of formula (II), chosen from diacids (D represents —OH) and the corresponding anhydrides thereof, in which $R^2$ is a divalent hydrocarbyl radical containing from 1 to 14, more preferably from 1 to 10 and even more preferably from 1 to 8 carbon atoms, limits inclusive, and
- at least one compound of formula (III), in which $R^7$ is a hydrocarbyl group containing 1 to 7, preferably 1 to 6 carbon atoms and more preferably 1 to 4 carbon atoms, A"O is ethoxy, and u and u' each represent 1, and also the products of total quaternization reaction thereof with methyl chloride.

Typical preferred compounds of formula (1) according to the present invention are those obtained by simultaneous/sequential/alternating esterification condensation reaction(s) of:
- at least one compound of formula (I) chosen from n-octylamine, n-decylamine, n-dodecylamine, (coconut-alkyl)amine, (palm oil-alkyl)amine, n-tetradecylamine, n-hexadecylamine, n-octadecylamine, oleylamine, (tallow-alkyl)amine, (hydrogenated tallow-alkyl)amine, (rapeseed-alkyl)amine, (soybean-alkyl)amine, erucylamine, alkoxylated with 2 to 20, preferably 2 to 10 EO (ethylene oxide units), and/or 2 to 20, preferably 2 to 10 PO (propylene oxide units),
- at least one compound of formula (II) chosen from malonic acid, succinic acid, glutaric acid, glutaconic acid, adipic acid, muconic acid, pimelic acid, phthalic acid and isomers thereof, tetrahydrophthalic acid, malic acid, maleic acid, fumaric acid, suberic acid, mesaconic acid, sebacic acid, azelaic acid, tartaric acid, itaconic acid, glutinic acid, citraconic acid, brassylic acid, dodecanedioic acid, traumatic acid, thapsic acid, the corresponding acid chlorides thereof, the corresponding methyl or ethyl esters thereof, and the corresponding cyclic anhydrides thereof, and also mixtures thereof, and
- at least one compound of formula (III) chosen from methyldiethanolamine, ethyldiethanolamine, propyldiethanolamine, butyldiethanolamine, isobutyldiethanolamine, pentyldiethanolamine, hexyldiethanolamine, heptyldiethanolamine, and also the corresponding alkoxylation products thereof, and also the products of partial or total quaternization reaction thereof.

More preferred compounds of formula (1) according to the present invention are those obtained by simultaneous/sequential/alternating esterification condensation reaction(s) of:
- at least one compound of formula (I) chosen from n-dodecylamine, (coconut-alkyl)amine, (palm oil-alkyl)amine, n-tetradecylamine, n-hexadecylamine, n-octadecylamine, oleylamine, (tallow-alkyl)amine, (hydrogenated tallow-alkyl)amine, (rapeseed-alkyl)amine, (soybean-alkyl)amine, erucylamine, alkoxylated with 2 to 20, preferably 2 to 10 EO (ethylene oxide units),
- at least one compound of formula (II) chosen from malonic acid, succinic acid, glutaric acid, glutaconic acid, adipic acid, muconic acid, pimelic acid, phthalic acid and isomers thereof, tetrahydrophthalic acid, malic acid, maleic acid, fumaric acid, suberic acid, mesaconic acid, sebacic acid, azelaic acid, tartaric acid, itaconic acid, glutinic acid, citraconic acid, brassylic acid, dodecanedioic acid, traumatic acid, thapsic acid, the corresponding acid chlorides thereof, the corresponding methyl or ethyl esters thereof, and the corresponding cyclic anhydrides thereof, and also mixtures thereof, and
- at least one compound of formula (III) chosen from methyldiethanolamine, ethyldiethanolamine, propyldiethanolamine, butyldiethanolamine, isobutyldiethanolamine, pentyldiethanolamine, hexyldiethanolamine, heptyldiethanolamine, and also the corresponding ethoxylation products thereof, and also the products of partial or total quaternization reaction thereof.

The most preferred compounds of formula (1) according to the present invention are those obtained by simultaneous/sequential/alternating esterification condensation reaction(s) of:
- at least one compound of formula (I) chosen from n-dodecylamine, (coconut-alkyl)amine, (palm oil-alkyl)amine, n-tetradecylamine, n-hexadecylamine, n-octadecylamine, oleylamine, (tallow-alkyl)amine, (hydrogenated tallow-alkyl)amine, (rapeseed-alkyl)amine, (soybean-alkyl)amine, erucylamine, alkoxylated with 2 to 20, preferably 2 to 10 EO (ethylene oxide units),
- at least one compound of formula (II) chosen from malonic acid, succinic acid, glutaric acid, adipic acid, pimelic acid, maleic acid, fumaric acid, suberic acid, sebacic acid, azelaic acid, brassylic acid, dodecanedioic acid, the corresponding cyclic anhydrides thereof, and
- at least one compound of formula (III) chosen from methyldiethanolamine, ethyldiethanolamine, propyldiethanolamine, butyldiethanolamine, isobutyldiethanolamine, pentyldiethanolamine, hexyldiethanolamine, heptyldiethanolamine, and also the products of total quaternization reaction thereof with methyl chloride.

The compounds of formula (1) according to the invention have many advantages, and among these advantages mention may be made of their preparation process, which is relatively easy to perform, even on an industrial scale. The majority of the compounds of formula (1) may be readily prepared from inexpensive and readily available starting materials.

The compound that may be obtained by esterification condensation of the alkoxylated fatty amine of formula (I) (comprising its product of partial or total quaternization), with the dicarboxylic acid, or a derivative thereof, of formula (II), and with an (alkyl)alkanolamine derivative of formula (III) (comprising its product of partial or total quaternization), and more particularly the compound of formula (1), as defined above and according to the present invention have numerous advantageous properties. Per se, it may be used, purely for illustrative purposes, and without any limitation, as surfactant, biocidal agent, anticorrosion agent, wetting agent, and the like.

Per se, the compound that may be obtained by esterification condensation of the alkoxylated fatty amine of formula (I) (comprising its product of partial or total quaternization), with the dicarboxylic acid, or a derivative thereof, of formula (II), and with an (alkyl)alkanolamine derivative of formula (III) (comprising its product of partial or total quaternization), and more particularly the compound of formula (1), as defined above may be used in various applications, among which mention may be made of uses as collector for ore enrichment (flotation), as a corrosion inhibitor, for example in the field of oil and gas production, as a viscosity enhancer, emulsifier or stabilizer that is useful for the oil and gas industry (as a demulsifier, surfactant for enhanced oil recovery, surfactant for fracturing fluids, surfactant for acidifying fluids, surfactant for improving the injectability of produced water, surfactant for drilling muds, and the like), as a clay modifier, as an adhesion promoter, as an antiagglomerant additive, for example in the field of oil and gas production, as an additive in haircare products, as a fabric softener, as an antistatic agent in polymers, as a bitumen emulsion additive, as a detergency cationic agent, for example in the field of industrial detergency, car washing, as a fertilizer additive, as an antiagglomerant for hydrates, as a lubrication or adhesion-promoting additive, and the like.

The invention will become more clearly apparent by means of the following examples, which are presented solely by way of illustration, without any intention of limiting the scope of the desired protection defined by the appended claims. Throughout the description, examples and claims, all the ranges of values should be understood as being "limits inclusive" (that is to say that the limits are included in said ranges), unless otherwise specified.

Process for Measuring the Acid Number:

Throughout the examples that follow, the acid number is measured by potentiometric titration using a potassium hydroxide solution as reagent and isopropyl alcohol as solvent.

About 10 g of sample to be analyzed are accurately weighed out (Sw, accuracy to within one mg) in a 250 ml beaker and 70 ml of isopropyl alcohol are added. The mixture is stirred and heated gently, if necessary, to obtain a homogeneous sample. The combined reference glass electrode of the titrator is introduced into the solution, which is then stirred with a magnetic stirrer. Acid-base titration of the sample is performed using aqueous 0.1N potassium hydroxide (KOH) solution and the change in pH is recorded on the titrator. The equivalence point is determined by graph using processes known to those skilled in the art, and the volume (VKOH, in ml) of potassium hydroxide solution used to reach this point is determined. The acid number (AV) is then obtained according to the following calculation:

$$AV = \frac{[\text{Normality of the } KOH \text{ solution (mol/L)}] \times 56.1 \times V_{KOH}}{Sw}$$

Process for Measuring the Total Alkalinity:

Throughout the examples that follow, the total alkalinity value is measured by potentiometric titration using a hydrochloric acid solution as reagent and isopropyl alcohol as solvent.

About 3 g of sample to be analyzed are accurately weighed out (accuracy to within one mg, Sw to within one g) in a 100 ml polypropylene beaker and 60 ml of isopropyl alcohol are added. The mixture is stirred and heated gently, if necessary, to obtain a homogeneous sample. Once the temperature of the solution has returned to room temperature, the combined reference glass electrode of the titrator is introduced into the solution, which is then stirred with a magnetic stirrer. The sample is titrated using a 0.2N hydrochloric acid (HCl) solution of accurately known normality (N, in $m_{eq}.ml^{-1}$), and the change in pH is recorded on the titrator. The equivalence point is determined using processes known to those skilled in the art, and the volume (VHCl, in ml) of hydrochloric acid solution used to reach this point is determined. The total alkalinity value (Alk) is then obtained according to the following calculation:

$$Alk(meq/g) = \frac{VHCL*n}{Sw}$$

Example 1

Synthesis of a Product A (According to the Invention)

1196.7 g (2.5 mol) of ethoxylated (5 EO) tallow-amine supplied by Arkema under the trade name Noramox® S5, 715.2 g (3.45 mol) of methyldiethanolamine (>99%) supplied by Taminco and 0.5 g of aqueous hypophosphorous acid solution at 50% by weight are placed in a 4 L round-bottomed flask.

The mixture is heated to 80° C. while sparging with nitrogen. The sparging is stopped and 756.8 g (5.18 mol) of adipic acid are then introduced with stirring.

After 15 minutes, the temperature of the mixture is increased to 120° C. over a period of 1 hour and the pressure in the tank is gradually reduced until a pressure of 6.66 kPa (50 mmHg) is reached. The temperature is increased to 190° C. and the temperature and pressure are maintained until virtually all the acid has been consumed (acid number <5).

The system is then cooled to recover 2482.3 g of crude orange/brown liquid reaction product containing the desired esteramine, the unreacted amines and the unreacted diacid.

Example 2

Synthesis of a Product B (According to the Invention)

1420.1 g (2.97 mol) of ethoxylated (5 EO) tallow-amine supplied by Arkema under the trade name Noramox® S5, 353.2 g (2.97 mol) of methyldiethanolamine (>99%) supplied by Taminco and 0.5 g of aqueous hypophosphorous acid solution at 50% by weight are placed in a 4 L round-bottomed flask.

The mixture is heated to 80° C. while sparging with nitrogen. The sparging is stopped and 650 g (4.45 mol) of adipic acid are then introduced with stirring.

After 15 minutes, the temperature of the mixture is increased to 160° C. and maintained for 4 hours. The temperature is then increased to 190° C. and the temperature and pressure are maintained until virtually all the acid has been consumed (acid number <5). The pressure in the tank is then gradually reduced until a pressure of 6.66 kPa (50 mmHg) is reached and the pressure and temperature are maintained for a further 2 hours.

Finally, the system is cooled and the pressure is returned to atmospheric pressure in order to recover 2260 g of crude orange/brown liquid reaction product containing the desired esteramine, the unreacted amines and the unreacted diacid.

Example 3

Synthesis of a Product C (According to the Invention)

2022 g of the esteramine product A obtained in Example 1 are placed in a 6 L glass reactor with 453 g of isopropyl alcohol. Methyl chloride is added until the pressure in the tank reaches 290 kPa. The temperature is maintained at 80° C.-85° C. until a complete reaction has taken place.

A complete reaction is obtained when the total alkalinity value is less than or equal to 0.2 $m_{eq}.g^{-1}$. The reactor is then allowed to cool to 65° C. and the pressure is returned to atmospheric pressure. Nitrogen is sparged into the mixture for 2 hours, after which 2095.9 g of the crude brown reaction product still containing 6.7% by weight of isopropyl alcohol are recovered.

Example 4

Synthesis of a Product D (Aaccording to the Invention)

1803.7 g of the esteramine product B obtained in Example 2 are placed in a 6 L glass reactor with 788.3 g of isopropyl alcohol. Methyl chloride is added until the pressure in the tank reaches 290 kPa. The temperature is maintained at 80° C.-85° C. until a complete reaction has taken place.

A complete reaction is obtained when the total alkalinity value is less than or equal to 0.2 $m_{eq}.g^{-1}$. The reactor is then allowed to cool to 65° C. and the pressure is returned to atmospheric pressure. Nitrogen is sparged into the mixture for 2 hours, after which 2206.6 g of the crude brown reaction product still containing 17.3% by weight of isopropyl alcohol are recovered.

Example 5

Synthesis of a Product E (According to the Invention)

595 g (5 M) of MDEA (methyldiethanolamine) and 6 g of KOH (aqueous solution at 50% by weight) are placed in a dry 4 L autoclave. The reactor is then closed and filled with a nitrogen atmosphere and the seal is protected against leaks. The MDEA and the catalyst are dehydrated to less than 1000 ppm of water. The pressure is then increased to 75 kPa and 25° C. with nitrogen. The temperature in the reactor is then increased to 90° C. with stirring. Next, the temperature is again increased to 120° C. and 40 g to 50 g of ethylene oxide are added. Additional ethylene oxide, for a total of 1100 g (25 M) in total, is added over 3 hours at 140° C.-150° C. After addition of the ethylene oxide, the reaction mixture is maintained at this temperature for 30 minutes ("cooking") and the liquid aqueous phase is then subjected to distillation under nitrogen. At the end of the reaction, the reactor is cooled to 60° C. and 1655 g of MDEA 5 EO are obtained.

1420.3 g (2.97 mol) of ethoxylated (5 EO) tallow-amine supplied by Arkema under the trade name Noramox® S5, 745.5 g (2.97 mol) of MDEA 5 EO (synthesized as described above) and 0.5 g of aqueous hypophosphorous acid solution at 50% by weight are placed in a 4 L round-bottomed flask.

The mixture is heated to 80° C. while sparging with nitrogen. The sparging is stopped and 650 g (4.45 mol) of adipic acid are then introduced with stirring.

After 15 minutes, the temperature of the mixture is increased to 160° C. and maintained for 4 hours. The temperature is then increased to 190° C. and the temperature and pressure are maintained until virtually all the acid has been consumed (acid number <5). The pressure in the tank is then gradually reduced until a pressure of 6.66 kPa (50 mmHg) is reached and the pressure and temperature are maintained for a further 2 hours.

Finally, the system is cooled and the pressure is returned to atmospheric pressure in order to recover 2654.5 g of crude orange/brown liquid reaction product containing the desired esteramine, the unreacted amines and the unreacted diacid.

Example 6

Synthesis of a Product F (According to the Invention)

2050 g of the esteramine product E obtained in Example 5 are placed in a 6 L glass reactor with 615 g of isopropyl alcohol. Methyl chloride is added until the pressure in the tank reaches 290 kPa. The temperature is maintained at 80° C.-85° C. until a complete reaction has taken place.

A complete reaction is obtained when the total alkalinity value is less than or equal to 0.2 $m_{eq}.g^{-1}$. The reactor is then allowed to cool to 65° C. and the pressure is returned to atmospheric pressure. Nitrogen is sparged into the mixture for 2 hours, after which 2496.9 g of the crude brown reaction product still containing 12.4% by weight of isopropyl alcohol are recovered.

Example 7

Synthesis of a Product G (According to the Invention)

510 g (5 M) of DMAPA (dimethylaminopropylamine) and 5 g (1% by weight) of water are placed in a dry 4 L autoclave. The reactor is then closed and filled with a nitrogen atmosphere and the seal is protected against leaks. The pressure is then increased to 100 kPa and 30° C. with nitrogen. The temperature in the reactor is then increased to 120° C. with stirring. 40 g of ethylene oxide are added. The temperature is increased linearly until the reaction begins. Additional ethylene oxide, for a total of 1100 g (25 M) in total, is added over 4 hours at 150° C.-160° C. After addition of the ethylene oxide, the reaction mixture is maintained at this temperature for 30 minutes ("cooking") and the liquid aqueous phase is then subjected to distillation under nitrogen. At the end of the reaction, the reactor is cooled to 60° C. and 1570 g of DMAPA 5 EO are obtained.

1196.1 g (2.5 mol) of ethoxylated (5 EO) tallow-amine supplied by Arkema under the trade name Noramox® S5, 805.4 g (2.5 mol) of DMAPA 5 EO (synthesized as described above) and 0.5 g of aqueous hypophosphorous acid solution at 50% by weight are placed in a 4 L round-bottomed flask.

The mixture is heated to 80° C. while sparging with nitrogen. The sparging is stopped and 547.9 g (3.75 mol) of adipic acid are then introduced with stirring.

After 15 minutes, the temperature of the mixture is increased to 160° C. and maintained for 4 hours. The temperature is then increased to 190° C. and the temperature and pressure are maintained until virtually all the acid has been consumed (acid number<5). The pressure in the tank is then gradually reduced until a pressure of 6.66 kPa (50 mmHg) is reached and the pressure and temperature are maintained for a further 2 hours.

Finally, the system is cooled and the pressure is returned to atmospheric pressure in order to recover 2413.9 g of crude orange/brown liquid reaction product containing the desired esteramine, the unreacted amines and the unreacted diacid.

Example 8

Synthesis of a Product H (According to the Invention)

2040 g of the esteramine product E obtained in Example 5 are placed in a 6 L glass reactor with 600 g of isopropyl alcohol. Methyl chloride is added until the pressure in the tank reaches 290 kPa. The temperature is maintained at 80° C.-85° C. until a complete reaction has taken place.

A complete reaction is obtained when the total alkalinity value is less than or equal to 0.2 $m_{eq} \cdot g^{-1}$. The reactor is then allowed to cool to 65° C. and the pressure is returned to atmospheric pressure. Nitrogen is sparged into the mixture for 2 hours, after which 2396.7 g of the crude brown reaction product still containing 12.9% by weight of isopropyl alcohol are recovered.

Example 9

Synthesis of Products I to R (According to the Invention)

According to the same process as in Example 1, the following products were prepared from the compounds indicated in Table 1 below:

TABLE 1 compounds and amounts used for synthesizing products I to R according to the invention

| Alkoxylated fatty amine of formula (I) | Weight of (I) (in g) | Dicarboxylic acid, or derivative, of formula (II) | Weight of (II) (in g) | (Alkyl)alkanolamine derivative of formula (III) | Weight of (III) (in g) | Product | Weight of product (in g) |
|---|---|---|---|---|---|---|---|
| NoxS5 | 717.7 | Ad. ac. | 657.5 | MDEA | 932.9 | I | 2145.6 |
| NoxS5 | 956.9 | Ad. ac. | 730.5 | MDEA | 829.2 | J | 2336.1 |
| NoxS5 | 1435.4 | Succ. anh. | 450.5 | MDEA | 621.9 | K | 2345.4 |
| NoxS5 | 1435.4 | Male. anh. | 441.5 | MDEA | 621.9 | L | 2336.2 |
| NoxS5 | 1435.4 | Seb. ac. | 909.9 | MDEA | 621.9 | M | 2804.5 |
| NoxS2 | 1039.4 | Ad. ac. | 657.5 | MDEA | 621.9 | N | 2156.3 |
| NoxS11 | 1446.4 | Ad. ac. | 438.3 | MDEA | 414.6 | O | 2190.8 |
| NoxC5 | 1320.9 | Ad. ac. | 657.5 | MDEA | 621.9 | P | 2437.7 |
| NoxS5 | 1435.4 | Ad. ac. | 657.5 | TEA | 447.6 | Q | 2378.1 |
| NoxS11 | 1446.4 | Ad. ac. | 438.3 | MDEA5OE | 502.0 | R | 2278.2 |

NoxS5 is an ethoxylated (5 EO) tallow-amine supplied by Arkema under the trade name Noramox ® S5
NoxS2 is an ethoxylated (2 EO) tallow-amine supplied by Arkema under the trade name Noramox ® S2
NoxS11 is an ethoxylated (11 EO) tallow-amine supplied by Arkema under the trade name Noramox ® S11
NoxC5 is an ethoxylated (5 EO) coconut-amine supplied by Arkema under the trade name Noramox ® C5
MDEA is methyldiethanolamine (>99%) supplied by Taminco
TEA is triethanolamine (>99%) supplied by Taminco
MDEA is methyldiethanolamine (>99%) supplied by Taminco
MDEA 5 EO is as described in Example 5
Ad. ac. denotes adipic acid, Succ. anh. denotes succinic anhydride and Male. anh. denotes maleic anhydride.

Example 10

Synthesis of Products S to AB (According to the Invention)

According to the same process as in Example 3, the chloromethyl quaternary ammonium derivatives of products I to R were prepared from the compounds indicated in Table 2 below:

TABLE 2 compounds and amounts used for synthesizing products S to AB according to the invention

| Reactive product | Weight of product (in g) | Weight of isopropanol (in g) | Product obtained | Weight of product obtained (in g) | Isopropanol content of the product (% by weight) |
|---|---|---|---|---|---|
| I | 1800.2 | 540.1 | S | 2187.7 | 14.8% |
| J | 1900.5 | 570.2 | T | 2255.1 | 13.9% |
| K | 1900.2 | 570.1 | U | 2286.4 | 14.2% |
| L | 1900.1 | 570.0 | V | 2258.0 | 13.1% |

TABLE 2-continued compounds and amounts used for synthesizing
products S to AB according to the invention

| Reactive product | Weight of product (in g) | Weight of isopropanol (in g) | Product obtained | Weight of product obtained (in g) | Isopropanol content of the product (% by weight) |
| --- | --- | --- | --- | --- | --- |
| M | 2200.3 | 660.1 | W | 2556.7 | 11.6% |
| N | 1800.4 | 540.1 | X | 2176.8 | 14.4% |
| O | 1800.1 | 540.0 | Y | 2111.6 | 12.8% |
| P | 2000.1 | 600.0 | Z | 2350.2 | 12.3% |
| Q | 2000.3 | 600.1 | AA | 2322.0 | 11.1% |
| R | 1800.4 | 540.1 | AB | 2142.7 | 14.1% |

The invention claimed is:

1. A compound which may be obtained by esterification condensation of:

A/ an alkoxylated fatty amine of formula (I), or the product of partial or total quaternization of said alkoxylated fatty amine of formula (I):

$$R^1{-}\underset{\underset{B}{|}}{N}{-}[(CH_2)_s{-}N]_y{-}\begin{matrix}(AO)_mH\\(AO)_nH\end{matrix} \quad (I)$$

in which:
R$^1$ is chosen from a hydrocarbyl group containing 8 to 24 carbon atoms, and a group of formula R$^4$—O-(A'O)$_w$-T-, in which R$^4$ is a hydrocarbyl group containing 8 to 24 carbon atoms, w represents an integer in the range from 0 to 20, A'O is an alkylenoxy group containing 2 to 4 carbon atoms, T is alkylene with 1 to 6 carbon atoms,
AO is an alkylenoxy group containing 2 to 4 carbon atoms,
B is chosen from a C$_1$-C$_4$ alkyl, an aryl and an arylalkyl group,
m represents an integer between 1 and 20, limits inclusive,
n represents an integer between 1 and 20, limits inclusive,
s is 1, 2 or 3, and
y is an integer from 0 to 5, B/ with a dicarboxylic acid, or a derivative thereof, of formula (II):

$$D{-}\underset{O}{\overset{}{C}}{-}R^2{-}\underset{O}{\overset{}{C}}{-}D \quad (II)$$

in which
D is chosen from —F, —Cl, Br and —OR$^3$, in which R$^3$ is hydrogen or a C$_1$-C$_4$ alkyl group,
R$^2$ is chosen from the group constituted by:
a direct bond,
a linear or branched, saturated or unsaturated C$_1$-C$_{20}$ hydrocarbon-based chain optionally substituted with one or more —OH groups, a substituted alkylene radical, said alkylene radical being substituted with 1 or 2 —OH groups, an alkenylene radical containing from 1 to 20 carbon atoms, a substituted alkenylene radical, said alkenylene radical being substituted with 1 or 2 methyl and/or methylene groups,
a cycloalkylene group,
cycloalkenylene and
arylene C/ with an (alkyl)alkanolamine of formula (III) derivative or product of partial or total quaternization of said (alkyl)alkanolamine derivative of formula (III):

$$R^7{-}N\begin{matrix}(A''O)_u{-}H\\(A''O)_{u'}{-}H\end{matrix} \quad (III)$$

in which:
A''O represents an alkylenoxy group containing from 2 to 4 carbon atoms,
u represents an integer between 1 and 20, limits inclusive,
u' represents an integer between 1 and 20, limits inclusive,
R$^7$ is chosen from a hydrocarbyl group containing 1 to 7, an aryl or arylalkyl group, a group of formula H—(OA'')$_v$- (in which v represents an integer between 1 and 20, limits inclusive), HO(CH$_2$)$_q$—, and a group of formula (IV):

$$\begin{matrix}R^8\\R^9\end{matrix}N{-}(CH_2)_q{-}, \quad (IV)$$

in which R$^8$ and R$^9$, which may be identical or different, are chosen from a hydrocarbyl group containing 1 to 6 carbon atoms, and q is an integer from 1 to 10, limits inclusive, or R$^8$ and R$^9$, together with the nitrogen atom to which they are attached, form a 5-, 6- or 7-membered ring, optionally including one or more heteroatoms chosen from oxygen, nitrogen and sulfur.

2. The compound as claimed in claim 1, in which the radical R$^1$ of the fatty amine of formula (I) includes 8 or more than 8 carbon atoms, limits inclusive, and the radical R$^7$ of the (alkyl)alkanolamine derivative of formula (III) includes 6 carbon atoms or less, limits inclusive.

3. The compound as claimed in claim 1, in which the radical $R^1$ and the radical $R^7$ of the fatty amine of formula (I) and of the (alkyl)alkanolamine derivative of formula (III), respectively, are such that the difference in the number of carbon atoms they include is greater than 2, limits inclusive.

4. The compound as claimed in claim 1, in which some or all of the nitrogen atoms also react with a reagent of formula $R^5X$, in which $R^5$ is chosen from a $C_1$-$C_6$ hydrocarbyl group, a phenyl and a phenylalkyl, group, and X is chosen from halogens, sulfates, carbonates, and the like.

5. The compound as claimed in claim 1, in which the alkoxylated fatty amine of formula (I) is of formula (IA):

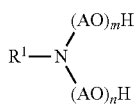

(IA)

which is the alkoxylated fatty amine of formula (I) in which y represents 0 and $R^1$, AO, m and n are as defined in claim 1,
and also the corresponding partially or totally quaternized derivatives thereof.

6. The compound as claimed in claim 1, in which the (alkyl)alkanolamine derivative of formula (III) is of formula (IIIA):

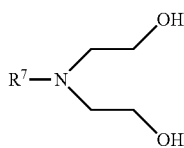

(IIIA)

which is the (alkyl)alkanolamine of formula (III) in which u and u' each represent 1, A"O is ethylenoxy and $R^7$ is as defined in claim 1,
and also the corresponding partially or totally quaternized derivatives thereof.

7. The compound as claimed in claim 1, in which the (alkyl)alkanolamine derivatives of formula (III) comprise, but are not limited to, triethanolamine, methyldiethanolamine, ethyldiethanolamine, propyldiethanolamine, butyldiethanolamine, isobutyldiethanolamine, pentyldiethanolamine, phenyldiethanolamine, hexyldiethanolamine, heptyldiethanolamine, and also the corresponding alkoxylation products thereof.

8. The compound as claimed in claim 1, in which the dicarboxylic acid derivative of general formula (II) is chosen from a dicarboxylic acid, a dicarboxylic acid halide, a dicarboxylic acid diester or a cyclic anhydride of a dicarboxylic acid.

9. The compound as claimed in claim 1, wherein the dicarboxylic acid derivatives of general formula (II) comprise oxalic acid, malonic acid, succinic acid, glutaric acid, glutaconic acid, adipic acid, muconic acid, pimelic acid, phthalic acid and isomers thereof, tetrahydrophthalic acid, malic acid, maleic acid, fumaric acid, suberic acid, mesaconic acid, sebacic acid, azelaic acid, tartaric acid, itaconic acid, glutinic acid, citraconic acid, brassylic acid, dodecanedioic acid, traumatic acid, thapsic acid, the corresponding acid chlorides thereof, the corresponding methyl or ethyl esters thereof, and the corresponding cyclic anhydrides thereof, and also mixtures thereof.

10. The compound as claimed in claim 1, in which the mole ratio between the reagents [(I)+(III)] and (II) is from 2:1 to 1:2.

11. The compound as claimed in claim 1, in which the mole ratio between the reagents [(I)+(III)] and (II) is from 2:1 to 1:1.

12. The compound as claimed in claim 1, in which the mole ratio between (I) and (III) is from 15:1 to 1:15.

13. A compound of general formula (1):

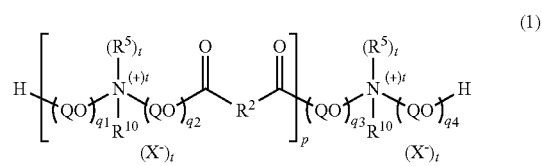

(1)

in which:
$R^2$ is chosen from:
  a direct bond,
  a linear or branched, saturated or unsaturated $C_1$-$C_{20}$ hydrocarbon-based chain optionally substituted with one or more —OH groups, a substituted alkylene radical, said alkylene radical being substituted with 1 or 2 —OH groups, an alkenylene radical containing from 1 to 20 carbon atoms, a substituted alkenylene radical, said alkenylene radical being substituted with 1 or 2 methyl and/or methylene groups,
  a cycloalkylene group,
  cycloalkenylene and
  arylene
$R^5$ is chosen from a $C_1$-$C_6$ hydrocarbyl group, a phenyl group and a phenylalkyl group,
X is chosen from halogens, sulfates, carbonates, and the like,
t is 0 or 1,
p is an integer in the range from 1 to 15,
QO represents an alkylenoxy group containing from 2 to 4 carbon atoms, given that all the Q groups present in the compound of formula (1) may be identical or different,
$q_1$, $q_2$, $q_3$ and $q_4$, which may be identical to or different from each other, each represent an integer between 1 and 20, limits inclusive,
each group $R^{10}$, independently of each other, represents $R^7$ or a group $R^1$-$(G)_y$-,
$R^7$ is chosen from a hydrocarbyl group containing 1 to 7, an aryl or arylalkyl group, a group of formula H—$(OA")_v$-(in which v represents an integer between 1 and 20, limits inclusive), $HO(CH_2)_q$—, and a group of formula (IV):

(IV)

in which $R^8$ and $R^9$, which may be identical or different, are chosen from a hydrocarbyl group containing 1 to 6 carbon atoms, and q is an integer from 1 to 10, limits inclusive, or $R^8$ and $R^9$, together with the nitrogen atom to which they are attached, form a 5-, 6- or 7-membered ring, optionally including one or more heteroatoms chosen from oxygen, nitrogen and sulfur, $R^1$ is chosen from a hydrocarbyl group containing 8 to 24 carbon atoms, and a group of formula $R^4$—O—$(A'O)_w$-T-, in which $R^4$ is a hydrocarbyl group containing 8 to 24 carbon atoms w represents an integer in the range from 0 to 20, A'O is an alkylenoxy group containing 2 to 4 carbon atoms, T is alkylene with 1 to 6 carbon atoms, y is an integer from 0 to 5, and G represents a group of formula (IV):

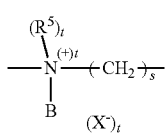

(IV)

in which $R^5$, X and t are as defined above,

B is chosen from a $C_1$-$C_4$ alkyl, an aryl and an arylalkyl group, and s is 1, 2 or 3, given that at least one of the groups $R^{10}$ represents $R^7$, and at least one other of the groups $R^{10}$ represents $R^1$-$(G)_y$- and each t is independent of the others.

14. The compound as claimed in claim 13, in which:

$R^2$ is chosen from the group consisting of a divalent hydrocarbyl radical containing from 1 to 10, limits inclusive, when $R^{10}$ is $R^7$, $R^7$ is chosen from a hydrocarbyl group containing 1 to 4 carbon atoms, when $R^{10}$ is $R^1$-$(G)y$-, y=0 and $R^1$ is chosen from a hydrocarbyl group containing 8 to 24 carbon atoms, QO represents an ethoxy group and p, $q_1$, $q_2$, $q_3$, $q_4$, t, $R^5$ and X are as defined in claim 13.

15. The compound as claimed in claim 13, in which all the "t" are equal to 1.

16. The compound as claimed in claim 13, which is obtained from simultaneous/sequential/alternating esterification condensation reaction(s) of:

at least one compound of formula (I), in which y=0 and $R^1$ is chosen from a hydrocarbyl group containing 8 to 24 carbon atoms, at least one compound of formula (II), and at least one compound of formula (III), in which $R^7$ is a hydrocarbyl group containing 1 to 7 and also the products of partial or total quaternization reaction thereof.

17. The use of a compound as claimed in claim 1 as a collector for ore enrichment (flotation), as a corrosion inhibitor, as a viscosity enhancer, emulsifier or stabilizer that is useful for the oil and gas industry, as a clay modifier, as an adhesion promoter, as an antiagglomerant additive, as an additive in haircare products, as a fabric softener, as an antistatic agent in polymers, as a bitumen emulsion additive, as a detergency cationic agent, as a fertilizer additive, as an antiagglomerant for hydrates, as a lubrication or adhesion-promoting additive, and the like.

* * * * *